United States Patent
Jarrousse et al.

(10) Patent No.: US 6,645,477 B1
(45) Date of Patent: Nov. 11, 2003

(54) USE OF METALLOPROTINEASE INHIBITORS TO INDUCING AND/OR STIMULATING GROWTH OF HAIR OR HAIR OR HAIRS AND/OR FOR SLOWING DOWN THEIR LOSS

(75) Inventors: Francoise Jarrousse, Livry-Gargan (FR); Yann Mahe, Morsang-sur-Orge (FR)

(73) Assignee: Societe L'Oreal S.A., Paris (FR)

( * ) Notice: Subject to any disclaimer, the term of this patent is extended or adjusted under 35 U.S.C. 154(b) by 0 days.

(21) Appl. No.: 09/700,195
(22) PCT Filed: May 11, 1999
(86) PCT No.: PCT/FR99/01124
§ 371 (c)(1),
(2), (4) Date: Feb. 20, 2001
(87) PCT Pub. No.: WO99/58101
PCT Pub. Date: Nov. 18, 1999

(30) Foreign Application Priority Data

May 12, 1998 (FR) .............................. 98 05968

(51) Int. Cl.$^7$ .................... A61K 7/06; C12N 15/15
(52) U.S. Cl. .................... 424/70.1; 435/69.2; 435/69.1; 435/183
(58) Field of Search .................. 424/70.1; 435/69.2; 435/69.1, 183

(56) References Cited

U.S. PATENT DOCUMENTS

| 4,814,351 | A | | 3/1989 | Mathews et al. |
| 5,618,925 | A | | 4/1997 | Dupont et al. |
| 6,025,334 | A | | 2/2000 | Dupont et al. |
| 6,028,118 | A | | 2/2000 | Dupont et al. |
| 6,166,005 | A | * | 12/2000 | De et al. ............... 514/211.1 |
| 6,380,366 | B1 | * | 4/2002 | Dupont et al. ............ 530/422 |

FOREIGN PATENT DOCUMENTS

| EP | 0335 554 A | 10/1989 |
| EP | 0414 605 A | 2/1991 |
| EP | 0455 422 A | 11/1991 |
| EP | 0797 978 A | 10/1997 |
| GB | 2321 852 A | 8/1998 |
| WO | 93 00079 A | 1/1993 |
| WO | 94 06459 A | 3/1994 |
| WO | 96 40185 A | 12/1996 |

OTHER PUBLICATIONS

"Chemical Abstracts"; 115:141 993, Colombus, OH & JP 03074318A (Mizumaki) Mar. 28, 1991 XP002091869.

"Chemical Abstracts"; 130:143 951; & JP 11029441A; Feb. 2, 1999; XP002110857.

"Chemical Abstracts"; 119:15 093; & JP 05043424A (Sansei Seiyaku et al) Feb. 23, 1993 XP002110858.

"Chemical Abstracts"; 120:86 083; & JP 05279230A (H. Ogawa et al) Oct. 26, 1993 XP002110859.

Greene et al, "Molecular Cloning and Characterization of Human Tissue Inhibitor of Metalloproteinase 4*", *The Journal of Biological Chemistry*, vol. 271, No. 48, pp. 30375–30380 (1996), published by The American Society for Biochemistry and Molecular Biology, Inc., Bethesda, MD.

Silbiger et al, Cloning of cDNAs encoding human TIMP–3, a novel member of the tissue inhibitor of metalloproteinase family, *Gene*, 141, pp. 293–297 (1994), published by Elsevier Science B.V., Oxford, United Kingdom.

Gomez et al, "Tissue inhibitors of metalloproteinases: structure, regulation and biological functions", *European Journal of Cell Biology* 74, pp. 111–122 (1997), published by Wissenschaftliche Verlagsgesellschaft, Sturttgart, Germany.

Woessner, Jr., "Matrix metalloproteinases and their inhibitors in connective tissue remodeling", *The FASEB Journal*, vol. 5, pp. 2145–2154 (1991), published by The Federation of American Societies for Experimental Biology, Bethesda, MD.

* cited by examiner

*Primary Examiner*—Raymond Henley, III
*Assistant Examiner*—Donna Jagoe
(74) *Attorney, Agent, or Firm*—Burns, Doane, Swecker & Mathis, L.L.P.

(57) ABSTRACT

The invention concerns the use in/for the preparation of a composition, as active principle in a physiologically acceptable medium, an efficient amount of at least a metalloproteinase inhibitor or any functional biological equivalent, for inducing and/or stimulating growth of hair or hairs and for slowing down their loss. The invention also concerns a method for the cosmetic treatment of hair or hairs.

24 Claims, No Drawings

USE OF METALLOPROTINEASE INHIBITORS TO INDUCING AND/OR STIMULATING GROWTH OF HAIR OR HAIR OR HAIRS AND/OR FOR SLOWING DOWN THEIR LOSS

The present invention relates to the use, in or for the preparation of a composition, as active principle in a physiologically acceptable medium, of an effective amount of at least one metalloprotease inhibitor, or of any functional biological equivalent, which is intended to induce and/or stimulate the growth of head hair or other hairs and/or to slow down their loss.

In humans, the growth and renewal of the hair are mainly determined by the activity of the hair follicles and by their dermo-epidermal environment. Their activity is cyclic and essentially comprises three phases, i.e. the anagenic phase, the catagenic phase and the telogenic phase.

The active anagenic phase or growth phase, which lasts for several years and during which the hair gets longer, is followed by a very short and transient catagenic phase which lasts a few weeks, and then comes a rest phase, known as the telogenic phase, which lasts a few months.

At the end of the rest period, the hair falls out and another cycle begins. The head of hair is thus under constant renewal, and out of the approximately 150,000 hairs which make up a head of hair, at any given moment, approximately 10% of them are at rest and will thus be replaced within a few months.

In a large number of cases, early hair loss occurs in individuals who are genetically predisposed, and it usually affects men. This more particularly concerns androgenetic or androgenic or even androgenogenetic alopecia.

This alopecia is essentially due to a disruption in hair renewal which leads, in a first stage, to an acceleration of the frequency of the cycles, at the expense of the quality of the hair and then at the expense of its quantity. A gradual depletion of the head of hair takes place by regression of the so-called "terminal" hairs at the downy stage. Regions are preferentially affected, in particular the temples or frontal bulbs and the back of the head in men, whilst in women diffuse alopecia of the vertex is observed.

Substances for suppressing or reducing alopecia, and in particular for inducing or stimulating hair growth or reducing hair loss, have been sought for many years in the cosmetics and pharmaceutical industries.

Admittedly, in this respect, a large number of very diverse active compounds have already been proposed, such as, for example, 2,4-diamino-6-piperidinopyrimidine 3-oxide or "Minoxidil" described in U.S Pat. No. 4,596,812, or the many derivatives thereof, such as those described, for example, in patent applications EP 0 353 123, EP 0 356 271, EP 0 408 442, EP 0 522 964, EP 0 420 707, EP 0 459 890 and EP 0 519 819.

Mention may also be made of 6-amino-1,2-dihydro 1hydroxy-2-imino-4-piperidinopyrimidine and its derivatives, which are described more particularly in patent U.S Pat. No. 4,139,619.

However, it would generally still be advantageous and useful to be able to provide active compounds other than those already known.

Now, after considerable research conducted in this matter, the Applicant has just discovered that a metalloprotease inhibitor, or any functional biological equivalent, makes it possible to induce and/or stimulate the growth of head hair or other hairs, and/or to reduce their loss in an effective manner.

Metalloproteases (MMPs) are members of a family of proteolitic enzymes (endoproteases) which contain a zinc atom coordinated to 3 cysteine residues and one methionine residue in their active site and which degrade the macromolecular components of the extracellular matrix and the basal sheets at neutral pH (collagen, elastin, etc.). These enzymes, which are very widely distributed in the living world, are present, but weakly expressed, in normal physiological situations such as organ growth and tissue renewal. However, their overexpression in man and their activation are associated with many processes which involve the destruction and remodelling of the matrix. This entails, for example, an uncontrolled resorption of the extracellular matrix.

Metalloproteases are produced and secreted in an inactive zymogenic form (pro-enzyme). These zymogenic forms are then activated in the extracellular environment by the removal of a propeptide region. The members of this family can activate each other.

Regulation of the activity of MMPs thus takes place at the level of the expression of the genes (transcription and translation), at the level of the activation of the zymogenic form, or at the level of the local control of the active forms.

The main regulators of the activity of MMPs are the tissue inhibitors of metalloproteases, or TIMPs. However, the expression of MMPs is also modulated by growth factors, cytokines, oncogenic products (ras, jun) or matrix constituents.

The metalloprotease family consists of several well-defined groups based on their resemblances in terms of substrate specificity and structure (see Woessner J. F., Faseb Journal, vol. 5, 1991, 2145). Among these groups, mention may be made of collagenases intended to degrade fibrillar collagens (MMP-1 or interstitial collagenase, MMP-8 or neutrophil collagenase, and MMP-13 or collagenase 3), gelatinases which degrade type IV collagen or any form of denatured collagen (MMP-2 or gelatinase A (72 kDa), MMP-9 or gelatinase B (92 kDa)), stromelysins whose broad spectrum of activity applies to extracellular matrix proteins such as glycoproteins (fibronectin, laminin), proteoglycans, etc. or alternatively membrane metalloproteases.

The Applicant has now discovered that metalloproteases are present in the internal structures of hair follicles, namely in the inner epithelial sheath (IRS). In particular, MMP-9 is found in the IRS.

Now, it is known that in the course of the hair cycle, hair follicles pass from a low-level location in the dermis in the anagenic phase, to a high-level location in the dermis during the telogenic phase. This movement should be accompanied by a change in the extracellular matrix which allows the migration of the follicle, this change possibly being due to an expression of the MMPs, bringing about a controlled degradation of the said extracellular matrix. It is at the end of the telogenic phase that hair loss occurs. However, it is also known that cytokines and growth factors have an influence on the hair cycle. For example, epidermal growth factor (EGF) promotes the in vitro transition from the anagenic phase to the catagenic phase (formation of a "club" structure characteristic of the catagenic phase), this being the phase which precedes the loss of the head hairs or other hairs. It is also known, as the Applicant has demonstrated, that there is an inflammatory phase in alopecia.

The Applicant has shown that the MMPs and particularly MMP-9, can be induced by interleukin-1 and/or EGF, in particular in the fibroblasts of the dermal papillae.

The advantage of reducing the expression of MMPs in the scalp in order to slow down or inhibit the degradation of the perifollicular matrix and thus to slow down or even prevent hair loss may thus be appreciated.

The Applicant thus proposes the use of metalloprotease inhibitors to induce and/or stimulate the growth of head hair or other hairs and/or to slow down their loss.

Thus, the invention relates to the use, in or for the preparation of a composition, of an effective amount of at least one metalloprotease inhibitor or of any functional biological equivalent, which is intended to induce and/or stimulate the growth of head hair or other hairs and/or to slow down their loss.

The expression "functional biological equivalent" means any molecule which is functionally equivalent in terms of biological function, at least one of the components of which may have been changed for an equivalent component.

Examples which may be mentioned are peptides, one biological equivalent of which may be a peptide in which at least one amino acid residue has been replaced with another amino acid having a similar hydropathic index.

The expression "metalloprotease inhibitor" means any molecule capable of regulating the activity of MMPs either at the level of the expression of the genes (transcription and translation) or at the level of the activation of the zymogenic form of MMPS, or alternatively at the level of the local control of the active forms.

The main regulators of the activity of MMPs are natural molecules present in the tissues, known as tissue inhibitors of metalloproteases, or TIMPs.

However, these inhibitors may also be known chemical molecules such as, for example, hydroxamic acid derivatives, cation-chelating agents, growth factors, cytokines, oncogenic products (ras, jun) or matrix constituents.

According to the invention, tissue inhibitors of metalloproteases (TIMPs) such as, for example, the peptides known in the prior art under the names TIMP-1, TIMP-2, TIMP-3 and TIMP-4 (Woessner J. F., Faseb Journal, 1991) are preferably used.

Thus, the invention relates more particularly to the use, in or for the preparation of a composition, of an effective amount of at least one tissue inhibitor of metalloproteases (TIMP) or of any functional biological equivalent, the inhibitor or the composition eing intended to induce and/or stimulate the growth of head hair or other hairs and/or to slow down their loss.

The peptides known in the prior art under the names TIMP-1, TIMP-2, TIMP-3 and TIMP-4 are preferably used according to the invention as tissue inhibitors of metalloproteases.

Needless to say, according to the invention, the metalloprotease inhibitors can be used alone or as a mixture.

It may be the case that, for reasons of resistance to degradation, it is necessary according to the invention to use a protected form of the metalloprotease inhibitor. The form of the protection should obviously be a biologically compatible form. Many biologically compatible forms of protection may be envisaged, such as, for example, acylation or acetylation of the amino-terminal end or amidation of the carboxy-terminal end.

Thus, the invention relates to a use as defined above, characterized in that the metalloprotease inhibitor is in a protected or unprotected form.

A protection based either on the acylation or acetylation of the amino-terminal end, or on the amidation of the carboxy-terminal end, or alternatively on both approaches, is preferably used according to the invention.

Among the chemical inhibitors which may be mentioned are thiols and hydroxamates.

The amount of metalloprotease inhibitor which can be used according to the invention obviously depends on the desired effect and should be in an amount which is effective to induce and/or stimulate the growth of head hair or other hairs and/or to slow down their loss.

By way of example, the amount of metalloprotease inhibitor which can be used according to the invention may range, for example from 0.01% to 5% and preferably from 0.05% to 2% relative to the total weight of the composition.

The composition is preferably a cosmetic composition.

The composition according to the invention can be administered enterally or parenterally. preferably, via the parenteral route, the composition is administered topically.

The physiologically acceptable medium in which the peptide is used according to the invention may be anhydrous or aqueous. The expression "anhydrous medium" means a solvent medium containing less than 1% water. This medium may consist of a solvent or a mixture of solvents chosen more particularly from $C_2$–$C_4$ lower alcohols such as ethyl alcohol, alkylene glycols such as propylene glycol, and alkylene glycol alkyl ethers or dialkylene glycol alkyl ethers, the alkyl or alkylene radicals of which contain from 1 to 4 carbon atoms. The expression "aqueous medium" means a medium consisting of water or of a mixture of water and another physiologically acceptable solvent, chosen in particular from the organic solvents mentioned above. In this last case, when these other solvents are present, they represent approximately 5% to 95% by weight of the composition.

It is possible for the physiologically acceptable medium to contain other adjuvants usually used in cosmetics, such as surfactants, thickeners or gelling agents, cosmetic agents, preserving agents, and acidifying and basifying agents that are well known in the prior art, and in amounts that are sufficient to obtain the desired presentation form, in particular a more or less thickened lotion, a gel, an emulsion or a cream. The composition can optionally be used in a form pressurized as an aerosol or vaporized from a pump-dispenser bottle.

It is also possible for the peptide to be used in combination with compounds for further improving the activity on hair regrowth and/or on slowing down hair loss, which have already been described for this activity.

Among the latter compounds, mention may be made more particularly, in a non-limiting manner, of:

nicotinic acid esters, in particular including tocopheryl nicotinate, benzyl nicotinate and $C_1$–$C_6$ alkyl nicotinates such as methyl or hexyl nicotinate;

pyrimidine derivatives, such as 6-amino-1,2-dihydro-1-hydroxy-2-imino-4-piperidinopyrimidine also known as "Minoxidil" and as described in U.S. Pat. No. 4 139 619;

antiandrogenic agents 5-reductase inhibitors;

OH-radical scavengers, such as dimethylsulfoxide;

peptides such as, for example, the tripeptide Lys-Pro-Val;

microorganism extracts, particularly bacterial extracts;

plant extracts.

Other compounds can also be added to the above list, namely, for example, phospholipids such as lecithin, linoleic acid, linolenic acid, salicylic acid and derivatives thereof described in French patent FR 2 581 542, for instance salicylic acid derivatives bearing an alkyl radical containing from 2 to 12 carbon atoms in position 5 of the benzene ring, hydroxycarboxylic or ketocarboxylic acids and esters thereof, lactones and the corresponding salts thereof, carotenoids, eicosatetraenoic and eicosatrienoic acids or esters and amides thereof, vitamin D and derivatives thereof.

The cosmetic composition according to the invention can be applied to the alopecic regions of the scalp and hair of an individual, and is optionally left in contact for several hours and is optionally to be rinsed out. For example, the cosmetic composition containing an effective amount of at least one metalloprotease inhibitor can be applied to the hair and the scalp in the evening, kept in contact throughout the night and optionally shampooed out in the morning. These applications can be repeated daily for one or more months depending on the individual.

Thus, a subject of the present invention is also a cosmetic process for treating the hair and/or the scalp, characterized in that it consists in applying a cosmetic composition containing an effective amount of at least one metalloprotease inhibitor to the hair and/or the scalp, in leaving this composition in contact with the hair and/or the scalp, and optionally in rinsing it off.

The treatment process has the characteristics of a cosmetic process since it improves the aesthetics of the hair by making it more vigorous and making it look better.

Examples will now be given by way of illustration, which should not in any way limit the scope of the invention.

EXAMPLE 1

Daily Lotion

| | |
|---|---|
| TIMP-1 | 0.01 g |
| TIMP-2 | 0.01 g |
| 2,4 Diaminopyrimidine 3-oxide | 0.75 g |
| 95° ethanol | 30 g |
| Fragrance | qs |
| Dyes | qs |
| Demineralized water | qs 100 g |

EXAMPLE 2

Liposomal Gel

| | |
|---|---|
| Natipide II[1] (i.e. 2 g of phospholipids) | 10 g |
| TIMP-2 | 0.025 g |
| Carbomer | 0.25 g |
| Triethanolamine | qs pH = 7 |
| Preserving agents | qs |
| Demineralized water | qs 100 g |

[1] Water/Alcohol/Lecithin mixture from the company Nattermann

What is claimed is:

1. A method for inducing and/or stimulating the growth of hair and/or slowing hair loss comprising applying to the hair and/or the scalp of an individual in need thereof, a topical composition comprising an effective amount of at least one tissue inhibitor of metalloproteases (TIMP) or a protected form thereof in a physiologically acceptable medium, leaving said composition in contact with the hair and/or the scalp for a sufficient time and optionally rinsing said composition from the treated area.

2. The method according to claim 1, wherein said at least one tissue inhibitor of metalloproteases is of natural origin.

3. The method according to claim 2, wherein said at least one tissue inhibitor of metalloproteases is a protected form thereof.

4. The method according to claim 3, wherein said protected form is protected by acylation or acetylation of the amino-terminal end.

5. The method according to claim 3, wherein said protected form is protected by arnidation of the carboxy-terminal end.

6. The method according to claim 3, wherein said protected form is protected by acylation or acetylation of the amino-terminal end and by amidation of the carboxy-terminal end.

7. The method according to claim 1, wherein said at least one tissue inhibitor of metalloproteases is present in an amount of between 0.01% and 5% relative to the total weight of the composition.

8. The method according to claim 1, wherein said at least one tissue inhibitor of metalloproteases is present in an amount of between 0.05% and 2% relative to the total weight of the composition.

9. The method according to claim 1, wherein said at least one tissue inhibitor of metalloproteases is of synthetic origin.

10. A method for inducing and/or stimulating the growth of hair and/or slowing hair loss comprising applying to the hair and/or the scalp of an individual in need thereof, a topical composition comprising an effective amount of at least one tissue inhibitor of metalloproteases (TIMP) selected from the group consisting of TIMP-1, TIMP-2, TIMP-3, TIMP-4 and the protected forms thereof in a physiologically acceptable medium, leaving said composition in contact with the hair and/or the scalp for a sufficient time and optionally rinsing said composition from the treated area.

11. The method according to claim 10, wherein said composition comprises TIMP-1.

12. The method according to claim 11, wherein said TIMP-1 is present in an amount of between 0.01% and 5 % relative to the total weight of the composition.

13. The method according to claim 10, wherein said composition comprises TIMP-2.

14. The method according to claim 13, wherein said TIMP-2 is present in an amount of between 0.01% and 5% relative to the total weight of the composition.

15. The method according to claim 10, wherein said composition comprises a mixture of tissue inhibitors of metalloproteases.

16. The method according to claim 15, wherein said mixture of tissue inhibitors of metalloproteases is present in an mount of between 0.01% and 5% relative to the total weight of the composition.

17. The method according to claim 15, wherein said composition comprises a mixture of TIMP-1 and TIMP-2.

18. The method according to claim 17, wherein said mixture of TIMP-1 and TIMP-2 is present in an amount of between 0.01% and 5% relative to the total weight of the composition.

19. The method according to claim 10, wherein said at least one tissue inhibitor of metalloproteases is a protected form thereof.

20. The method according to claim 19, wherein said protected form is protected by acylation or acetylation of the amino-terminal end.

21. The method according to claim 20, wherein said protected form is protected by amidation of the carboxy-terminal end.

22. The method according to claim 21, wherein said protected form is protected by acylation or acetylation of the amino-terminal end and by amidation of the carboxy-terminal end.

23. The method according to claim 10, wherein said at least one tissue inhibitor of metalloproteases is present in an amount of between 0:01% and 5% relative to the total weight of the composition.

24. The method according to claim 10, wherein said at least one tissue inhibitor of metalloproteases is present in an amount of between 0.05% and 2% relative to the total weight of the composition.

* * * * *